| United States Patent [19] | [11] Patent Number: 4,477,567 |
| Healy et al. | [45] Date of Patent: Oct. 16, 1984 |

[54] CONTINUOUS BOVINE BETA CELL LINE

[75] Inventors: George M. Healy, Downsview; Anthony M. Sun, Willowdale; Hilda G. Macmorine, Thornhill, all of Canada

[73] Assignee: Connaught Laboratories Limited, Willowdale, Canada

[21] Appl. No.: 856,284

[22] Filed: Dec. 1, 1977

[51] Int. Cl.$^3$ .................. C12P 21/04; C12N 5/00
[52] U.S. Cl. ....................................... 435/71; 435/240
[58] Field of Search .................. 195/1.8; 435/71, 240

[56] References Cited
U.S. PATENT DOCUMENTS 4,225,671  9/1980  Puchinger ..................... 435/71

OTHER PUBLICATIONS

Chick et al.—Science, vol. 187, (Mar. 7, 1975), pp. 847 & 848.
Chick et al.—Endocrinology, vol. 92, No. 1, (1973), pp. 212, 213, 216–218.

*Primary Examiner*—Frederick E. Waddell
*Attorney, Agent, or Firm*—Sim & McBurney

[57] ABSTRACT

A new cell line which is morphologically very similar to the beta cell of the Islets of Langerhans is obtained by transformation of pancreatic bovine cells. The transformed cells contain the diploid number of chromosomes for the bovine species and produce insulin which may be extracted.

4 Claims, No Drawings

CONTINUOUS BOVINE BETA CELL LINE

FIELD OF INVENTION

The present invention relates to novel continuous cell lines, in particular to a transformed continuous bovine beta cell line, cultures thereof, a method for obtaining and culturing the continuous cell line and a method of producing insulin from the cultured cells.

BACKGROUND TO THE INVENTION

Since the discovery of insulin by Banting and Best in 1921, the hormone, for human use, has been extracted from the pancreata of domestic animals, mainly cattle and pigs. While the supply of pancreas has been sufficient for industry needs to the present time, there has always been a desire for an alternative supply of the hormone. Thus, complete chemical synthesis has been achieved but is time-consuming and very expensive when compared to extraction of the natural tissue. The functional units of the pancreas that produce and mediate the production of insulin are the Islets of Langerhans. Although the Islets of Langerhans are numerous, they are widely dispersed throughout the pancreatic tissue and constitute only 5% of the total cells of the whole organ. Within each islet of the three different constituent cell types, alpha, beta and delta, it is known that only the beta cell produces insulin, while the alpha and delta cells produce glucagon and gastrin respectively.

In the present state of the art of animal cell culture, there is a central dogma that normal somatic cells from higher animals, when cultivated outside the body, progress through three phases (see L. Hayflick, Experimental Cell Research. 37: 614, (1965)). Phase I is an induction period during which the cells become adjusted and in which there is limited or no growth. Phase II is a period of exponential growth, where only a finite number of population doublings are possible and this doubling potential is characteristic of the species, i.e. approximately 50 doublings for man and for cattle approximately 12 doublings, etc. A normal, homogenous, cell population in Phase II is called a "cell strain" and a necessary condition for multiplication during this phase is attachment to a surface, when growth proceeds in two dimensions (monolayers). Because of the limited number of doublings of normal cells, most cell strains are started from foetal tissue, thus allowing the maximum number of population doublings before the cells enter Phase III which is near the ultimate population doubling and when the cells become moribund and soon die. Occasionally in late Phase II, a genotypic and phenotypic alteration occurs when new cells appear that grow in fluid suspension and replicate indefinitely. Such a population, when homogenous, is termed a "cell line".

The present invention provides a novel continuous cell line that is morphologically very similar to the beta cell of the Islets of Langerhans and which is capable of producing insulin. The continuous cell line is obtained by transformation of bovine pancreas cells and has the unusual feature that they contain the diploid number of chromosomes for the bovine species (2n=60). Most transformed cells contain either more or fewer chromosomes than the normal cell.

A continuous cell line in accordance with this invention has been designated CLL 36A/76 and is deposited with American Type Culture Collection of Rockville, Md., under accession number ATCC CRL 1407. Although this indicated public availability is the simplest method of obtaining a cell line in accordance with this invention, it is not altogether impossible and improbable that similar and functionally identical bovine beta cell lines may be produced by procedures other than those described herein. Such functionally and morphologically substantially identical cell lines are equivalent to cell line 36A/76 and are included within the scope of this invention.

The continuous cell line is generally provided as a cell culture of the cell line in a nutrient culture medium. The nutrient culture medium preferably is that known by the trademark CMRL-1969.

CMRL-1969 is a well known nutrient culture medium whose properties and composition are described in detail in G. M. Healy et al., Applied Microbiology, vol. 21, 1 (1971). Although this material is identified by trademark, this is sufficient description for a person skilled in this art to identify the nutrient medium adopted.

The CMRL-1969 may be supplemented in the cell culture by calf serum, preferably foetal calf serum.

The insulin which is produced by the cell line may be extracted from centrifuged cells of the cell line by conventional biochemical extraction, for example, using acidic alcohol solvent. The insulin is readily recovered in solid form from the solvent.

The continuous cell line is produced from bovine pancreas tissue. The majority of the exocrine tissue is first removed from pancreatic tissue obtained from a viable calf embryo. The cells are transferred to a specific growth medium and allowed to become confluent.

These primary tissues are judged by observation and production of insulin as to whether they are essentially homogenous or are a mixture of cell types. If homogenous, the cells are propagated by standard methods in tissue culture flasks, or occasionally, if large numbers of cells are desired, in a multi-surface cell propagator(MSCP). Usually, shortly after the 12th passage the cells enter Phase III and die. Occasionally, in about 3% of such attempts, cells in Phase III do not die but undergo transformation into the cell line of this invention.

While the transformation of the Phase III cells into the cell line occurs in only about 3% of the cultures, the transformation nevertheless does occur in a repetitive manner. The transformation of Phase III cells into a continuous cell line according to this invention, is reproducible, although perhaps somewhat tedious to effect. The continuous cell line of this invention, therefore, results from a transformation of Phase III cells which occurs in a low percentage of attempts, rather than from a single chance transformation as is commonly the case with cell line formation.

Throughout Phase II of the propagation of the cells, application of known secretagogues, such as glucagon, to the cell cultures will stimulate the release of insulin into the medium, and the insulin may be separated by selective membrane (AMICON) filtration well-known to the art. After the cell line has formed, it no longer secretes insulin into the medium.

EXAMPLES

Example I

At the time of slaughter a viable calf embryo was obtained, the pancreas dissected out and trimmed free of fat mesentery and connective tissue. The pancreas was then distended using a modified form of medium CMRL-1969, that is calcium and magnesium-free. The distended tissue was transferred to a glass Petri dish with an approximately equal quantity of modified medium, and chopped into small fragments (approximately 1 to 2 mm$^3$). The mixture was washed twice with the same calcium and magnesium-free medium.

The washed fragments were transferred in calcium and magnesium-free CMRL-1969 containing 3.75 mg/ml of collagenase and 2.5 mg/ml of hyaluronidase to a 25 ml Erlenmeyer flask containing a stirring magnet. Using the lowest speed possible of the stirrer, the mixture was allowed to digest at 37° C. for 10 minutes, was transferred to a centrifuge tube and centrifuged at about 1000 rpm for ten minutes. The supernatant fluid was discarded and the packed cell mass resuspended in calcium and magnesium-free CMRL-1969 containing 0.25% crude trypsin (1:250). The suspension was transferred to a 25 ml Erlenmeyer flask containing a stirring magnet and was digested with slow stirring at 37° C. for about 8 minutes.

The cells and islets released by the crude trypsin digestion were transferred to a centrifuge tube and washed and resuspended three times with complete CMRL-1969 supplemented with 7.5% foetal calf serum, 200 mg % d-glucose, 0.36% hydroxyethyl piperazine (HEPES) buffer and 20 mcg/ml Gentamicin. The cell suspension was inoculated into several 25 cm$^2$ Falcon tissue culture flasks in 10 ml of the above complete medium and the flasks incubated at 37° C. Over a period of three to four weeks, the primary (Phase I) cultures should become confluent. Observation, using the inverted microscope, and radioimmune assay (RIA) testing of the spent medium for insulin content, determine which cultures are to be continued to obtain the cell strain. Thus, islets are readily recognized when viewed microscopically by indirect illumination and beta cells can be seen migrating as polyhedral cells with cytoplasmic granules and a central nucleus containing three to four nucleoli. After the first 10 to 14 days, the medium on selected cultures was changed every week and the spent medium assayed for insulin using RIA techniques. Insulin values of 200 to 2000 microunits/ml and direct observation of beta cells were justification for proceeding further with the experiment. RIA values of less than 100 microunits/ml and the presence of many fibroblasts overgrowing the beta cells show equivocal primary cultures and these were terminated.

When the selected primary cultures were confluent, the cells were harvested by trypsinization, a well-known procedure, to yield three to four million cells. These cells were washed as before and inoculated into two 25 cm$^2$ Falcon flasks. In addition, several Leighton tubes containing cover slips were inoculated and these were incubated along with the main cultures. The cells growing on the cover slips were used for distinctive tests, for insulin and for chromosome analysis and these techniques were used to advantage to monitor the main culture. Every seven to ten days, a subcultivation of the cultures, at a split ratio of 2:1 was performed, and this period of about 2 months corresponded to Phase II of the cell strain. Because of the large number of flasks required as the cells replicated, the MSCP was used for propagation after a certain number of doublings. This single apparatus is the equivalent of 1024 Falcon flasks, each of 25 cm$^2$ area (which would be required for the 10th doubling), and requires only 1/5th of the amount of medium.

Shortly after the twelfth passage the cells entered Phase III, usually became quiescent and eventually died. Occasionally, the cell strains achieved in Phase III did not die and round cells appeared on the monolayers. These cells were buoyant, multiplied in suspension and replicated indefinitely in the medium. The overall frequency of this random, spontaneous transformation was 3%.

The transformed cells contained the diploid number of chromosomes for the bovine species (2n=60), and many metacentric and submetacentric chromosomes in the complement. The cell line exhibited a morphology very similar to the beta cell of the Islets of Langerhans and had a generation time of not more than about 24 hours.

The use of medium CMRL-1969 was found to be highly desirable to the invention. Several other media, known to those skilled in the art, such as Eagle's MEM and Ham's F-12, were tried in comparative experiments and were shown to be inferior in the support of the cell cultures.

Example II

A cell strain was prepared following the procedure of Example I and the strain was passaged until it was well into Phase II (6th to 8th passage). At this point the medium was replaced by the normal growth medium containing additional secretagogues. The new medium was sampled immediately and again on the day following and the samples assayed for insulin content. Various secretagogues known to the art were used and the results are reproduced in the following Table.

TABLE

| | STIMULATION OF INSULIN SECRETION | | |
|---|---|---|---|
| | MICRO UNITS OF INSULIN PER ONE ML | | |
| Type of Challenge | One Day Prior to Challenge | Day of Challenge | One Day Post Challenge |
| Glucose, 100 mg/100 ml | 3.9 | 6.6 | 8.5 |
| Glucose, 300 mg/100 ml | 5.2 | 8.1 | 6.7 |
| Theophylline, 1 mM Glucose, 300 mg/100 ml | 12.1 | 2.6 | 8.7 |
| Arginine, 5 mM Glucose, 300 mg/100 ml | 78.3 | 6.2 | 7.5 |
| Tolbutamide, 130 µg/ml Glucose, 300 mg/100 ml | 5.4 | 3.6 | 7.5 |
| Glucagon, 20 µg/ml Glucose, 300 mg/100 ml | 5.4 | 3.0 | 806.2 |
| Glucagon 20 µg/ml, Theophylline 1 mM Glucose, 300 mg/100 ml | 3.2 | 2.1 | 700.3 |
| Glucagon, 20 µg/ml, Tolbutamide 130 µg/ml Glucose, 300 mg/100 ml | 2.5 | 2.2 | 634.1 |
| Glucagon, 20 µg/ml, Arginine 5 mM | 5.0 | 2.0 | 967.0 |

TABLE-continued

| STIMULATION OF INSULIN SECRETION | | | |
|---|---|---|---|
| | MICRO UNITS OF INSULIN PER ONE ML | | |
| Type of Challenge | One Day Prior to Challenge | Day of Challenge | One Day Post Challenge |
| Glucose, 300 mg/100 ml | | | |

It will be seen from the results of the above Table that the addition of glucagon to the medium greatly improves the secretion of insulin from the cell strain into the medium.

Example III

A transformed continuous cell line was prepared following the procedure of Example I and designated cell line 36A/76. At the fifteenth passage, the transformed cells were seeded into a spinner suspension culture, using the defined medium CMRL-1969 with the required supplements as detailed. The seed was in a 10:1 split ratio. After growing to the stationary phase, the cells were harvested by centrifuging and the entire cell mass was extracted with cold acid/ethanol in a manner known to those skilled in the art. A total of 18,000 milliunits (18 units) of insulin was obtained from 8 litres of suspension culture cells. Similar high yields of extractable insulin from continuous cell line 36A/76 were achieved through to the 26th passage (14 passages posttransformation).

SUMMARY

The present invention, therefore, provides a novel bovine beta cell line capable of producing insulin. Modifications are possible within the scope of the invention.

We claim:

1. A process for the production of insulin, which comprises:
    cultivating a continuous beta cell line as deposited with the American Type Culture Collection under accession number ATCC CRL 1407 in a nutrient culture medium for a time sufficient to form insulin in cells of the cell line,
    said cell line being characterized by transformed cells which:
    (1) have a morphology very similar to that of beta cells of the bovine pancreas,
    (2) have the diploid number of chromosomes for the bovine species,
    (3) have a generation time of not more than 24 hours,
    (4) are capable of producing insulin within the cells, and
    (5) do not secrete said produced insulin to the culture medium; and
    extracting insulin from cells of said cell line.

2. The process of claim 1 wherein said cells are extracted with an acidic alcohol solvent and insulin is isolated in solid form from the solvent.

3. The process of claim 1 wherein said nutrient growth medium is CMRL-1969.

4. The process of claim 3 wherein said nutrient growth medium is supplemented with foetal calf serum.

* * * * *